United States Patent [19]

Bonutti

[11] Patent Number: 5,033,457
[45] Date of Patent: Jul. 23, 1991

[54] AIR ASSISTED MEDICAL DEVICES

[76] Inventor: Peter M. Bonutti, 1303 W. Evergreen Plz., Effingham, Ill. 62401

[21] Appl. No.: 370,895

[22] Filed: Jun. 23, 1989

[51] Int. Cl.$^5$ .............................................. A61H 1/00
[52] U.S. Cl. ................................ 128/25 R; 128/24 R
[58] Field of Search ................ 128/24 R, 25 R, 25 B, 128/33; 272/130, 900

[56] References Cited

U.S. PATENT DOCUMENTS

| | | | |
|---|---|---|---|
| 2,245,909 | 6/1941 | Enfiajian | 128/33 X |
| 2,998,817 | 9/1961 | Armstrong | 128/33 |
| 3,492,988 | 2/1970 | De Mare . | |
| 3,795,242 | 3/1974 | Lerch et al. | 128/64 |
| 3,811,431 | 5/1974 | Apstein | 128/64 |
| 3,821,951 | 7/1974 | Giles | 128/25 B X |
| 3,982,531 | 9/1976 | Shaffer | 128/24 R |
| 4,003,374 | 1/1977 | Mizrachy | 128/25 R X |
| 4,248,421 | 2/1981 | Salazar | 272/130 |
| 4,343,302 | 8/1982 | Dillon | 128/24 R |
| 4,370,975 | 2/1983 | Wright | 128/64 |
| 4,418,690 | 12/1983 | Mummert | 128/24 R |
| 4,558,692 | 12/1985 | Greiner | 128/25 B X |
| 4,573,453 | 3/1986 | Tissot | 128/64 |
| 4,596,240 | 6/1986 | Takahashi et al. . | |
| 4,635,931 | 1/1987 | Brännstam | 128/25 B X |
| 4,671,258 | 6/1987 | Barthlome . | |
| 4,865,020 | 9/1989 | Bullard | 128/24 R X |
| 4,867,140 | 9/1989 | Hovis et al. | 128/24 R |

Primary Examiner—Richard J. Apley
Assistant Examiner—Linda C. M. Dvorak
Attorney, Agent, or Firm—Tarolli, Sundheim & Covell

[57] ABSTRACT

An air assisted device for positioning or moving a limb or a joint uses compressed air as a motive force. In a first embodiment, the air assisted device is a one piece air bag with bellows or accordion-like construction to allow controlled variable degrees of abduction. The bag is placed between a limb to be positioned and a relatively fixed body part or other surface. As compressed air enters the bag, the bag expands and moves the limb away from the body part or other surface. If the bag is maintained in an expanded condition, it immobilizes the limb relative to the body part or other surface. As the bag deflates, the limb returns to its original position. In a second embodiment, the device utilizes a pneumatic piston and cylinder unit to provide the motive force for positioning two relatively movable parts. As compressed air is forced into the cylinder, the piston moves outwardly, moving one of the relatively movable parts away from the other part. Relative movement of the parts moves the limb toward or away from the body part or other surface. The air assisted device may also be used to resist motion of a limb.

4 Claims, 2 Drawing Sheets

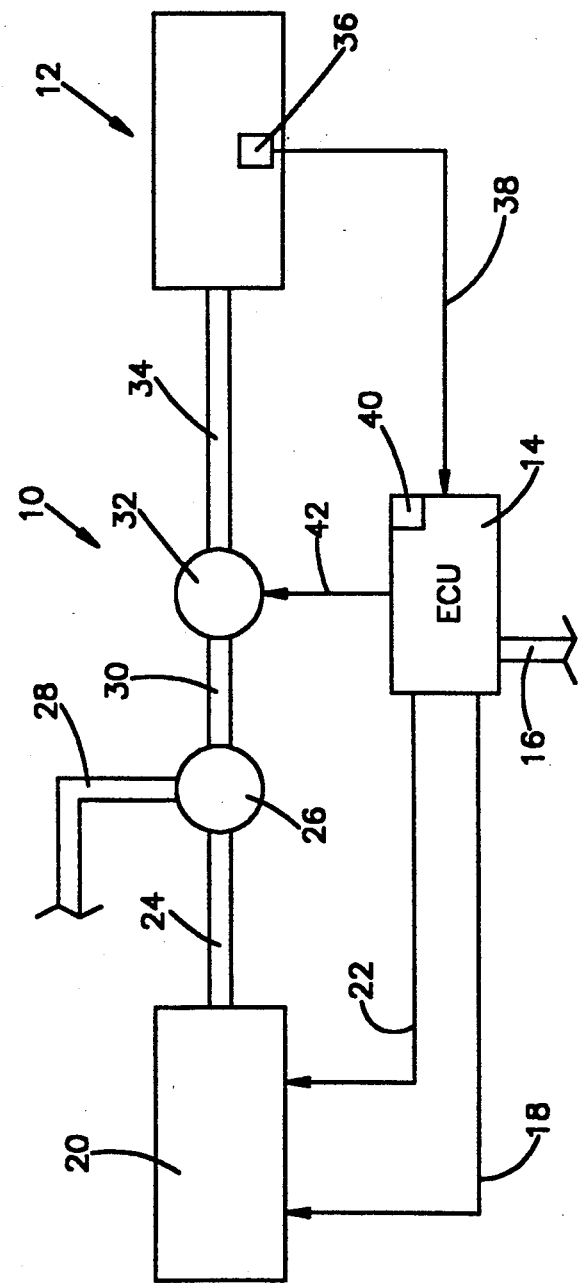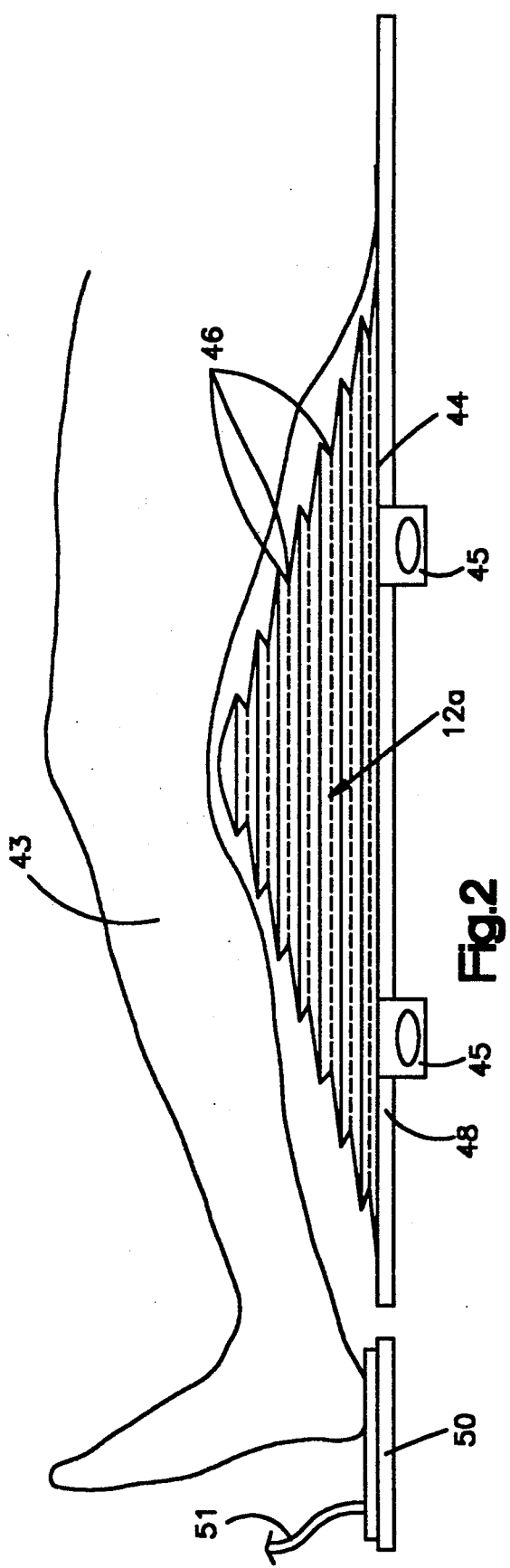

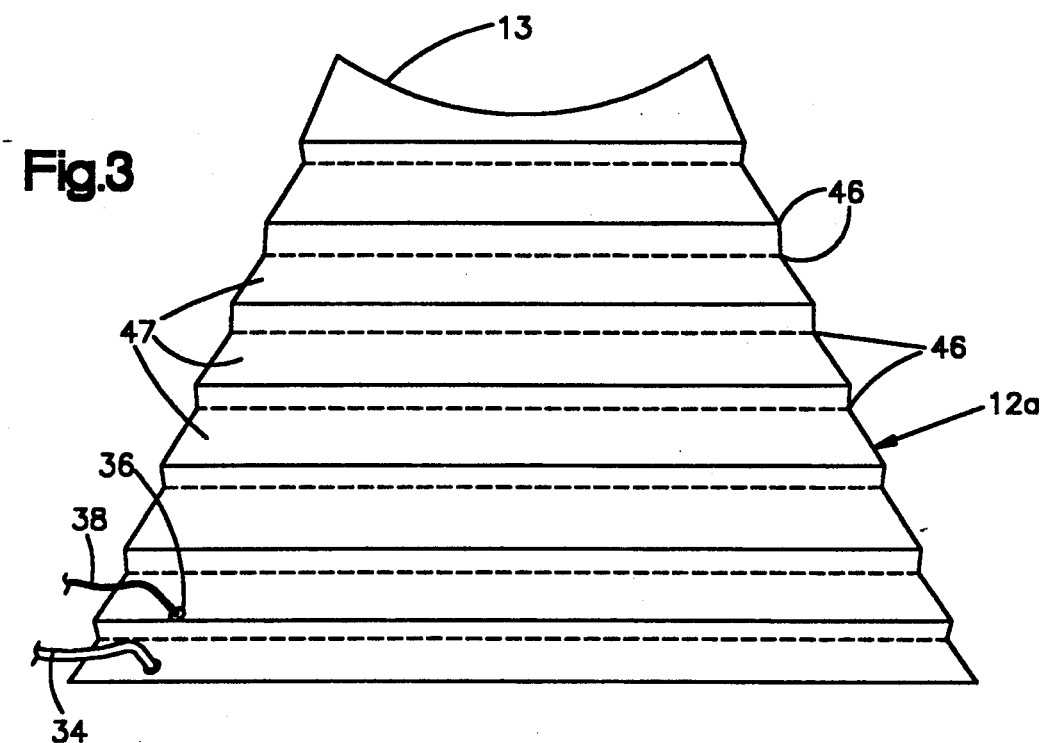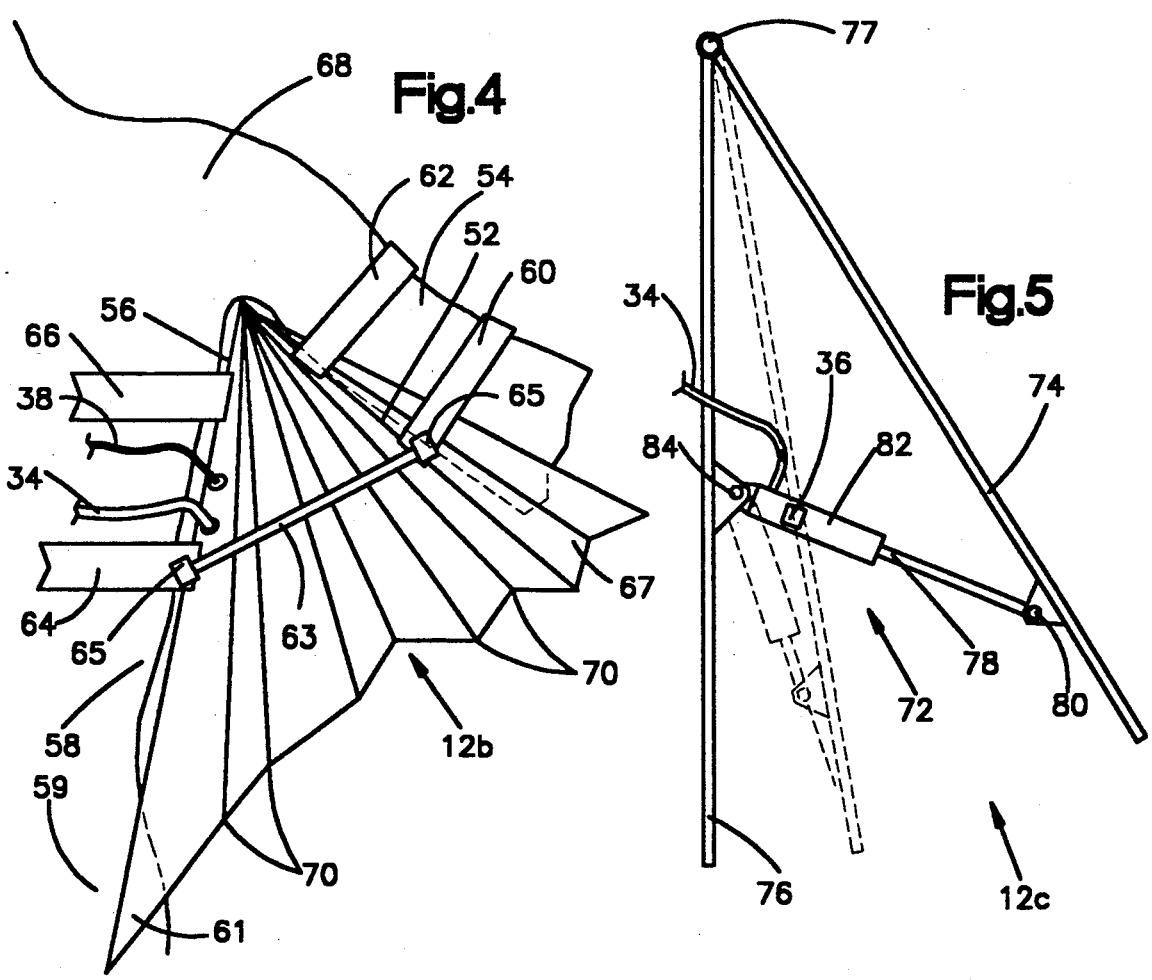

AIR ASSISTED MEDICAL DEVICES

BACKGROUND OF THE INVENTION

The present invention relates to medical devices for use in the positioning and movement of limbs or joints. More particularly, the present invention relates to air assisted devices which are capable of providing continuous passive motion asssistance or immobilization for stabilization or fracture fixation.

Typical devices used for providing continuous passive motion for joints and limbs, such as motor and cable arrangements, are bulky and awkward. Typical devices for immobilization of joints, such as casts, orthoses, custom splints, and abduction pillows, are heavy, and difficult and uncomfortable to wear. None of the devices in current use are simple, comfortable, and inexpensive.

SUMMARY OF THE INVENTION

The present invention is an air assisted device for positioning or moving a limb or a joint. The device is lightweight, comfortable and easy to wear and use, and relatively inexpensive. The device uses compressed air as a motive force. The device may be used either to assist motion of a limb or to resist motion of a limb.

In a first embodiment of the invention, the air assisted device is a one piece air bag with bellows or accordion-like construction to allow controlled variable degrees of expansion. In its unexpanded state, the bag is collapsed and occupies very little space. The unexpanded bag is placed between a limb to be positioned and a relatively fixed body part or other surface. As air under pressure enters the bag, the bag expands and moves the limb away from the body part or other surface. If the bag is maintained in an expanded condition, it immobilizes the limb relative to the body part or other surface. As the bag deflates, the limb returns to its original position. The particular shape of the bag is custom fit for the particular application for which the bag is to be used, i.e., positioning a shoulder joint, a knee joint, etc., or immobilizing a particular limb.

In a second embodiment of the invention, the air assisted device utilizes a pneumatic piston and cylinder unit to provide the motive force for positioning two relatively movable parts. The piston and cylinder unit is disposed between two parts which are preferably hingedly connected. The piston is connected to one of the parts and the cylinder is connected to the other part. The air device is placed between a limb to be positioned and a relatively fixed body part or other surface. As air under pressure enters the cylinder, the piston moves outwardly, moving one of the relatively movable parts away from the other part. Relative movement of the parts moves the limb toward or away from the body part or other surface. If the piston and cylinder unit is maintained in an expanded condition, it immobilizes the limb or joint. As the air is released from the cylinder, the limb returns to its original position. The two relatively movable parts are formed to have a particular shape, i.e., custom fit for the particular application for which the device is to be used.

BRIEF DESCRIPTION OF THE DRAWINGS

Further features of the present invention will become apparent upon a consideration of the following description taken in connection with the accompanying drawings, wherein:

FIG. 1 is a schematic illustration of a system including an air assisted device in accordance with the present invention;

FIG. 2 is a schematic end view of an air bag for use in a system as shown in FIG. 1, the air bag being shown in the deflated condition and designed for providing continuous passive motion to a knee joint;

FIG. 3 is a schematic end view of the air bag of FIG. 2 in an inflated condition;

FIG. 4 is a schematic illustration of an air bag usable for a shoulder joint; and FIG. 5 is a schematic illustration of an air assisted device in accordance with the present invention and incorporating a piston and cylinder arrangement.

DESCRIPTION OF SPECIFIC PREFERRED EMBODIMENTS OF THE INVENTION

FIG. 1 illustrates schematically a system 10 which supplies air under pressure for predetermined periods of time to move parts of an air assisted device 12 relative to each other. The system 10 includes an electronic control unit 14 connected to a source of electricity 16. The electronic control unit 14 controls through wiring 18 a compressor 20. The compressor 20 is powered by electric power supplied from the control unit 14 via wiring 22. The compressor 20 under the control of the control unit 14 compresses ambient air and supplies the compressed air through a supply pipe 24 to a supply valve 26. The supply valve 26 is optionally connected to a fixed source 28 of pressurized air such as, for example, a pressurized air line in a hospital room. The system 10 may thus be operated with a provided source 28 of pressurized air, or may supply its own pressurized air via the compressor 20.

Pressurized air from the supply valve 26 passes through piping 30 to a control valve 32. From the control valve 32, a supply line 34 leads to the air assisted device 12. The control valve 32 may, if desired, be constructed within or on the device 12. A pressure sensor 36 in or on the device 12 senses the air pressure in the device 12 and provides a control signal via wiring 38 to the electronic control unit 14. The electronic control unit 14 also includes a timer 40 which is settable to supply air to the device 12 for any predetermined period of time, and thus for cycling the operation of the device 12. The electronic control unit provides control signals via line 42 to the control valve 32 to regulate the air supply to the device 12.

The electronic control unit 14 includes a programmable microprocessor. The control unit 14 is programmed to supply air to the device 12 for predetermined periods of time, in order to move apart the relatively movable parts of the device 12 a certain distance over a certain period of time. The control unit 14 also controls the control valve 32 to release air from the device 12 in accordance with a predetermined pattern. The time duration and sequence is set by the patient or by medical personnel in order to provide the needed therapy. The control unit 14 including the sensor means 36 and the timer 40, by controlling the compressor 20 and the valve 32 and thus the air pressure and time of supply of the air, may provide any desired range of motion to the device 12.

In a first embodiment of the invention, the device 12a is a one-piece air bag having accordion-like ridges spaced thereabout to provide for controlled expansion of the air bag. FIGS. 2 and 3 illustrate schematically an air bag 12a in, respectively, almost completely deflated and inflated conditions, FIG. 3 being an end view of the bag 12a. The airbag 12a is shaped to fit under a knee joint 43 and is shaped with a recess 13 to receive the leg. As air is supplied under pressure, the air bag 12a expands from the condition shown in FIG. 2 to the inflated condition shown in FIG. 3 to flex the knee joint 43. Sensor means 36 senses the air pressure inside the bag 12a and outputs a signal through line 38 back to the control unit 14. The air bag 12a has a relatively flat base 44 for stability. Loops or attachments 45 receive straps for securing the bag 12a to an underlying bed (not shown). Straps may also be provided to prevent lateral movement of the bag 12a, especially when the bag 12a is in an intermediate position (i.e., semi-inflated). The straps may be inelastic or elastic and may be attached either to the bed or to the leg, or may be part of (formed as) a filament within the bag 12a itself.

The bag 12a is continuously inflated and deflated to provide continuous passive motion to the knee joint 43 for therapy purposes. The bag 12a operates on relatively low air pressure, for safety and for light weight and portable construction. The medical uses for which the device 12a is used, rapid motion is not generally necessary, and accordingly the low operating pressure of the system 10 is suitable. If the outside pressurized air supply 28 (FIG. 1) is of a higher pressure than needed, the pressurized air supplied therefrom may be passed through a pressure reducer valve (not shown) prior to being supplied to the remainder of the system 10.

The air bag 12a, upon the supply of pressurized air thereto, expands in an accordion-like manner (as a bellows). The material of which the bag 12a is made does not necessarily stretch although it may somewhat, but rather the expansion comes primarily when the various surfaces of the bag 12a are repositioned relative to one another. Various fabrics or plastics may be utilized to form the bag 12a. The material of which the bag 12a is made is preferably a light weight polymeric material. The preferred material is Mylar, reinforced with Kevlar, nylon, or graphite polyethylene, or metal filaments as now used in surgical gloves. The material must be selected to, first, retain pressurized air therein, and to retain a particular shape when inflated. The accordion-like ridges 46 may be made of differing degrees of resistance to straightening and flexing, in order to vary the rate and/or sequence of expansion of various portions of the bag 12a. Alternatively, the material of which the bag 12a is made has areas of rigidity interleaved with areas of more elasticity, to provide the desired expansion effect. The material may also be designed to be self-sealing, like an automobile tire.

Incoming air under pressure is supplied for a period of time as determined by the control unit 14. As the incoming air is supplied, the bag 12a expands from its deflated condition shown in FIG. 2 to its inflated condition shown in FIG. 3. When the supply of incoming air is to be stopped in accordance with the preset timer 40, the control unit 14 operates the two-way valve 32 to allow air to pass out of the bag 12a through the pipe 34 and the valve 32. The air is forced from the bag 12a by gravity, i.e., the weight of the leg pressing the bag 12a back to its deflated condition. The valve 32 is controllable to provide a variable resistance to air outflow therethrough, in order to vary the deflation rate of the bag 12a. Thus, the bag 12a may be maintained in its inflated condition as shown in FIG. 3, or in a semi-inflated condition intermediate that of FIGS. 2 and 3, for any period of time as desired.

Increasing the amount of air in the bag 12a results in further flexion of the knee joint 43. As the bag 12a is inflated from its condition shown in FIG. 2 to its fully inflated condition shown in FIG. 3, the bag 12a passes through a range of intermediate positions during which the knee joint 43 is flexed to varying degrees. The degree of flexion, and the amount of time required to attain that degree of flexion, are thus controllable by means of the control unit 14 with its timing capabilities. The pressure within the air bag 12a is easily regulated to provide exact control of the degree of flexion and extension of the joint 43, a capability not provided by the typical motor and cable arrangement. The system 10 provides a pulsatile airflow which forces air into the bag 12a for a set period of time, then shuts off, allowing deflation of the bag 12a. This cycling operation provides the continuous passive motion which is desired for exercise and therapy of the joint 43.

There may be used in conjunction with the bag 12a a base unit 48 disposed between the base 44 of the bag 12a and a relatively fixed surface, such as a hospital bed (not shown), on which the patient is disposed. The base unit 48 is either a separate inflatable portion of the bag 12a, or a separate attachable air bag. The base unit 48 may accordingly be varied in thickness by filling with more or less air, to limit the degree of extension of the knee joint 43, i.e., to provide an initial degree of flexion. Alternatively the base unit 48 may be a board or other kind of prop placed underneath the air bag 12a. Similarly, a foot piece 50 may be placed underneath the patient's foot and ankle to provide proper positioning thereof during the providing of continuous passive motion to the knee joint 43. The foot piece 50 may be a separate unit, or it may be a part of the air bag 12a. The foot piece 50 may be a further inflatable portion of the bag 12a or may be separately inflatable through an air supply line 51. The patient's foot may thus be raised relative to the surface on which the person is resting, in order to force full extension of the knee joint 43. FIG. 2 shows the bag 12a in an almost completely deflated condition, and the knee joint 43 is almost completely extended.

FIG. 4 illustrates schematically an air bag 12b which is designed and fitted for use in immobilization or passive motion assistance of a shoulder joint 68. The bag 12b has a first surface 52 which is fitted for contact with the arm 54 of the patient, and a second surface 56 which is fitted for contact with the relatively fixed torso 58 of the patient. The bag 12b is attached to the upper arm 54 by means of straps 60 and 62 using, for example, a VELCRO-type fastening. The bag 12b may also have VELCRO-type fastening to attach to the patient's shirt or other garment, since the bag 12b is so light in weight. The bag 12b is attached to the torso 58 by straps 64 and 66 fitting around the torso 58 to secure the bag 12b in position.

Controlled supply of pressurized air into and out of the bag 12b by means of the air supply pipe 34 moves the first surface 52 relative to the second surface 56 and therefore moves the upper arm 54 relative to the torso 58 about the shoulder joint 68. A plurality of accordion-like ridges 70 interconnect the first and second surfaces 52 and 56. The accordion-like ridges 70 provide controlled expansion of the air bag 12b and positioning of the first surface 52 relative to the second surface 56. Because the bag 12b, like the bag 12a shown in FIGS. 2 and 3, is made of a light weight plastic or fabric-type material, it may, in all instances, be fitted to closely conform to the surfaces which it contacts.

The surface 52 of the bag 12b is shaped to conform to the shape of the upper arm 54. Similarly, the surface 56 of the bag 12b is shaped to conform to the shape of the torso 58. The bag 12b, and specifically the first surface 52 thereon, is curved or extended at 67 to fit around the arm 54 in a form-fitting relationship. This is similar to the recess 13 in the bag 12a (FIG. 3), and further assists in maintaining proper positioning of the bag 12b relative to the arm 54. The second surface 56 of the bag 12b is similarly shaped as at 61 to fit the torso 58 or hip 59 to assist in maintaining the positioning of the bag 12b relative to the torso 58. One or more bars 63 securable with VELCRO straps at 65 to the bag 12a or to the arm 54 or torso 58 may be used to stabilize the bag 12 in any particular position for immobilization purposes.

In an alternative construction, the ridges 46 are closure members which divide the air bag 12 into a plurality of separately inflatable chambers 47 with valving (not shown) therebetween, for sequential inflation. Thus, as one chamber 47 fills, a valve leading to the next chamber 47 opens and that chamber then fills. In addition or separately, the chambers 47 may themselves have different rates of expansion in order to vary the sequence of expansion, i.e., an easily inflated chamber would fill before a chamber which fills only upon high air pressure therein.

The accordion-like or bellows construction of the air bag 12 provides significant advantages over a plain or unstructured air bag. The air bag 12 provides better control of the expansion (inflation) and contraction (deflation) characteristics by virtue of the structural rigidity and strength imparted by the accordion-like construction. An air bag which is not so constructed will expand in all directions at once or in whatever direction of expansion encounters the least resistance. Thus, depending on the particular application, a plain air bag would not provide the range of motion needed for the medical purposes for which the air bag is used. An air bag 12 constructed in accordance with the present invention also has far greater stability in intermediate (i.e., partially expanded) positions; collapses and deflates in a more uniform and regular manner, always returning to the same position or condition to assist in maintaining proper positioning of the patient; and has greater structural integrity. In this latter regard, the air bag 12a may be reinforced as with extra weaving or thicknesses of material or with strengthening elements at structurally important areas to increase strength and stability.

The air bags 12a and 12b which are shown schematically in FIGS. 2, 3 and 4 are illustrative examples of the many types of air bags which may be constructed and used in accordance with the present invention. Thus, it can be seen that an air bag in accordance with the present invention may be custom-shaped and fitted for use on a shoulder joint, a knee joint, an ankle, an elbow, a wrist, a hip, or any other part of the body wherein continuous passive motion or abduction is desired. Each air bag has appropriate fixation means such as straps or loops to secure it to the adjacent body part, such as the pelvis, thigh, knee, tibia, or foot, and, if appropriate, means for attaching it to a bed.

An air bag 12 may, as noted, also be used for immobilization of a joint. For such use, the bag 12 is expanded to a certain condition and then held in that condition. The bag 12a or 12b is fixed in position between a body part to be immobilized and a relatively fixed surface such as the torso, inflated to a certain degree, then closed to maintain that particular degree of inflation, in order to immobilize the joint or limb in question. In such case, the air bag is preferably separate or detachable from the remainder of the system 10 and portable with the patient. The air bag of the present invention is also thus useful for stabilization of a joint and fracture fixation of a limb, in addition to providing continuous passive motion for flexion and extension of joints.

The air bag 12 may advantageously be used in conjunction with a known pulsatile stocking which is attached to a leg or arm to promote blood flow in the leg or arm. Since both devices operate off of a pressurized air supply, the two devices may beneficially be used in conjunction with each other and operated from the same air supply to promote blood flow in the limb while the limb is in motion.

FIG. 5 illustrates schematically a second embodiment of the invention in which an air device 12c employs a pneumatic piston and cylinder unit 72 as the motive force for relatively positioning two relatively movable parts 74 and 76. The parts 74 and 76 may be hingedly connected at 77. A piston 78 is pivotally connected at 80 to the first relatively movable part 74, while a cylinder 82 is pivotally connected at 84 to the second relatively movable part 76. Air is supplied under pressure to the cylinder 82 by an air flow pipe 34. Both the first and second relatively movable parts 74 and 76 are, for example, custom-fitted plastic pieces which are shaped or shapable to conform to the surfaces which they contact, for example, the limb of the patient, or the torso, or a bed surface.

The device 12c is connected in the system 10 in lieu of the air bag 12a or 12b. Controlled supply of air under pressure into and out of the cylinder 82 positions the parts 74 and 76 relative to each other and provides the capability of a continuous range of motion therebetween. Air under pressure is supplied for a selected period of time in order to move the part 74 relative to the part 76 for a selected period of time over a selected distance. Air is then released from the cylinder 82 for a selected period of time in order to reposition the parts 74 and 76 under the influence of gravity. A pressure sensor 36 may be provided in the cylinder 82 for the purposes as described above.

The piston and cylinder unit 72 has a high mechanical advantage and thus operates on low air pressures. The availability of light weight, compact pneumatic cylinders lends itself to the use of such a product to position the relatively movable parts 74, 76. Such a device is accordingly portable and comfortable and easy to use by a patient. It should be noted that the relatively movable parts 74 and 76 need not be hingedly or pivotally connected, but may be connected by any flexible means such as fabric panels and in a closed (like the bag 12) or open fashion. The piston and cylinder unit 72 serves as the motive force for moving or positioning a body part relative to another body part or another surface. The relatively movable parts 74 and 76 thus need only be firm enough to transmit the motive force of the unit 72 to the body parts.

The air bag 12c may also be used for active motion purposes. That is, rather than to assist motion of the arm 54 away from the torso 58, the system 10 is set up so that the bag 12c resists motion of the arm 54 toward the torso 58. Appropriate timing of the air inlet and air outlet to the bag 12c, in conjunction with controlling the air outflow through the valve 32, provides a device which also resists the patient's attempts to deflate the bag 12c and thus bring the arm 54 back towards the torso 58. Accordingly, the patient must exert positive effort to accomplish the task, against the resistance of the air in the bag 12c. Such effort against resistance provides a different form of therapy for the patient, to wit, exercise. When the air bag 12b is so used, a separate outflow valve (not shown) is preferably provided. The outflow valve preferably has a variable orifice to provide varying degrees of resistance to air flow therethrough. The compressor 20 is used to inflate the bag 12b, then air is forced out manually through the outflow valve. Alternatively, the bag 12b is also inflated manually. Thus configured as an exercise device, the air bag 12b is especially useful when detached from the remainder of the system 10. The system 10 including the air bag 12c may also or alternatively be set to provide resistance to the patient's effort to move the arm 54 away from the torso 58, thus exercising a different set of muscles. These variations in the system 10 are of course usable with any air bag 12 or any air device 12 as described herein, not merely with the shoulder-type air bag 12b. Thus, variable-resistance exercise devices for any number of joints and limbs are easily and conveniently provided.

From the above description of a preferred embodiment of the invention, those skilled in the art will perceive improvements, changes and modifications. Such improvements, changes and modifications within the skill of the art are intended to be covered by the appended claims.

I claim:

1. Apparatus for assisting or resisting movement of a body part relative to a relatively fixed surface comprising a one-piece expandable air bag for placement between the body part and the relatively fixed surface and having first and second relatively movable surfaces, said first surface for contact with the body part, said second surface for contact with the relatively fixed surface, accordion-like expansion means interconnecting said first and second relatively movable surfaces for assisting or resisting movement of said first surface relative to said second surface upon varying the amount of air in said air bag, control means for controlling the amount of air in said air bag and means for supplying pressurized air into said air bag, wherein said means for controlling includes valve means for controlling flow of air into and out of said air bag and settable timer means for controlling the flow of air into and out of said airbag in accordance with a predetermined time sequence, and wherein said accordion-like expansion means includes a plurality of expansion means portions having differing degrees of flexibility to vary the rate of relative movement of separate portions of said air bag.

2. Apparatus for assisting or resisting movement of a body part relative to a relatively fixed surface comprising a one-piece expandable air bag for placement between the body part and the relatively fixed surface and having first and second relatively movable surfaces, said first surface for contact with the body part, said second surface for contact with the relatively fixed surface, and accordion-like expansion means interconnecting said first and second relatively movable surfaces for assisting or resisting movement of said first surface relative to said second surface upon varying the amount of air in said air bag, wherein said accordion-like expansion means includes first and second expansion means portions having differing degrees of flexibility to vary the rate of relative movement of separate portions of said air bag.

3. Apparatus as defined in claim 10 wherein said accordion-like expansion means defines a plurality of chambers in said air bag.

4. Apparatus as defined in claim 3 wherein at least two of said plurality of chambers have different rates of expansion.

* * * * *

UNITED STATES PATENT AND TRADEMARK OFFICE
CERTIFICATE OF CORRECTION

PATENT NO. : 5,033,457

DATED : July 23, 1991

INVENTOR(S) : Peter Mark Bonutti

It is certified that error appears in the above-identified patent and that said Letters Patent is hereby corrected as shown below:

Column 8, Line 34, Claim 3, delete "10" and
            insert --2--.

Signed and Sealed this

Tenth Day of November, 1992

*Attest:*

DOUGLAS B. COMER

*Attesting Officer*     Acting Commissioner of Patents and Trademarks